United States Patent [19]
Denis et al.

[11] Patent Number: 5,670,701
[45] Date of Patent: Sep. 23, 1997

[54] PREPARATION OF ALKYL ADIPATES

[75] Inventors: Philippe Denis, Decines; Jean-Michel Grosselin, Francheville; Jean Jenck, Chassieu; Francois Metz, Vernaison; Paul Rouyer, Lyons, all of France

[73] Assignee: Rhone-Poulenc Chimie, Courbevoie Cedex, France

[21] Appl. No.: 199,544

[22] Filed: Feb. 18, 1994

Related U.S. Application Data

[63] Continuation of Ser. No. 980,237, Nov. 23, 1992, abandoned.

[30] Foreign Application Priority Data

Nov. 21, 1991 [FR] France ................................ 91 14605

[51] Int. Cl.$^6$ ........................................... C07C 67/36
[52] U.S. Cl. ............................................. 560/204
[58] Field of Search ................................ 560/204

[56] References Cited

FOREIGN PATENT DOCUMENTS 0080957 8/1983 European Pat. Off. .
0301450 1/1989 European Pat. Off. .
2384738 10/1978 France .

OTHER PUBLICATIONS

Akio Matsuda, "The Cobalt Carbonyl-catalyzed Hydroesterification of Butadiene with Carbon Monoxide and Methanol", Bulletin of the Chemical Society of Japan, vol. 46 (1973), pp. 524–530.

*Primary Examiner*—Johann Richter
*Assistant Examiner*—Michael B. Hydorn
*Attorney, Agent, or Firm*—Burns, Doane, Swecker & Mathis, L.L.P.

[57] ABSTRACT

The alkyl adipates are prepared by reacting admixture consisting essentially of alkyl 3-pentenoate and alkyl 2-pentenoate with carbon monoxide and an alcohol, at elevated temperature, under superatmospheric pressure and in the presence of a catalytically effective amount of cobalt or a cobalt compound and a nitrogenous heterocyclic base.

2 Claims, No Drawings

PREPARATION OF ALKYL ADIPATES

This application is a continuation of application Ser. No. 07/980,237, filed Nov. 23, 1992 now abandoned.

BACKGROUND OF THE INVENTION

1. Field of the Invention

The present invention relates to the preparation of alkyl adipates by reacting carbon monoxide and an alcohol with particular admixture of alkyl pentenoates.

2. Description of the Prior Art

It is well known to this art, according to the *Bulletin of the Chemical Society of Japan*, 46, pp. 524–530 (1973), that a mixture containing certain dialkyl esters and especially an alkyl adipate is prepared by reacting carbon monoxide and an alcohol with an alkyl 3-pentenoate at high pressure and elevated temperature, in the presence of cobalt carbonyl and of a heterocyclic nitrogenous base, for example pyridine.

It is also well known to this art, per this same reference, that an alkyl 3-pentenoate is prepared by reacting carbon monoxide and an alcohol with butadiene at high pressure and elevated temperature in the presence of cobalt carbonyl and of a heterocyclic nitrogenous base, for example pyridine.

It too has been described (cf. French Patent No. 2,356, 622) to prepare alkyl 3-pentenoates by reacting carbon monoxide and an alcohol with butadiene contained in a $C_4$ cut at a carbon monoxide pressure of 300 to 1,000 bar at a temperature of 100° to 160° C., in the presence of a catalyst system based on cobalt and of a heterocyclic nitrogenous base such as pyridine or a related compound. The methyl 3-pentenoate yield is on the order of 95%. Numerous other publications exist describing, inter alia, enhancing the performance (activity and/or selectivity) of the reaction of conversion of an alkyl 3-pentenoate into an alkyl adipate, or facilitating the recycling of the cobalt-based catalyst in both of the reactions under study, or recovering the desired adipate in the crude product of the second reaction, or attenuating the pressure conditions of the first such reaction.

Exemplary such techniques include:

(a) the process described in French Patent No. 2,384,738, wherein a first stage thereof butadiene is converted into an alkyl 3-pentenoate under conditions which are similar to those indicated above, followed by separating a fraction of the tertiary nitrogenous bases and the excess hydrocarbons from the reaction mixture. In a second stage, the alkyl 3-pentenoate remaining in the reaction mixture is converted into a mixture of diesters in which the alkyl adipate predominates. The first stage is carried out at temperatures ranging from 80° to 150° C. at pressures of 300 to 2,000 bar; the second stage is carried out at temperatures ranging from 140° to 200° C. at pressures of 100 to 400 bar;

(b) the process described in European Patent No. 60,734, wherein said first stage is carried out in the presence of a palladium-based catalyst;

(c) the process described in European Application No. 192,340, wherein the cobalt concentration in said first stage is increased to permit substantially decreasing the pressure required for its satisfactory performance and to enable conducting said second stage in sequence (in series) without removing any constituent of the reaction mixture originating from the first stage;

(d) the process described in European Patent No. 80,957, entailing carrying out the second stage by beginning with an alkyl 2-pentenoate, and (e) the process described in European Patent Application No. 177,641, comprising regenerating the deactivated, cobalt-based catalyst by contacting a mixture thereof with a strongly acidic ion exchange resin before it is recycled to the reaction.

This latter process would appear to present a dual option, namely:

(i) removing the N-methylpyridinium ions (product of deactivation of the catalyst system), and (ii) replacing the lost acidity.

According to such treatment, a large fraction of the deactivated cobalt may be reactivated; a large fraction of the pyridine is thus removed from the carbonylation system (first and/or second stage). Thus, one must compensate for this chemical loss by addition of "fresh" pyridine to the system.

Such loss is problematical on an industrial scale in consideration of the fact that, in the second stage (conversion of the alkyl 3-pentenoate), it would correspond substantially to the cobalt stoichiometry employed and when it is accepted that the physical losses of pyridine (or another nitrogenous heterocyclic base) which are unavoidable on an industrial scale during the various treatments (extraction, distillation, purges, etc.) must also be considered.

SUMMARY OF THE INVENTION

Accordingly, a major object of the present invention is the provision of an improved process for the preparation of alkyl adipates by reacting carbon monoxide and an alcohol with an alkyl pentenoate, in which the chemical loss of the nitrogenous heterocyclic base is substantially reduced, while substantially maintaining the other performances of the reaction (activity, selectivity for adipate, etc.).

Briefly, the present invention features, in a first embodiment thereof, a process for the preparation of alkyl adipates by reacting carbon monoxide and an alcohol with an alkyl pentenoate at a pressure above atmospheric pressure and at an elevated temperature, in the presence of a catalytically effective amount of cobalt or a cobalt compound and of a nitrogenous heterocyclic base, said alkyl pentenoate comprising admixture consisting essentially of alkyl 3-pentenoate and 2-pentenoate.

This invention also features a process for the preparation of alkyl adipates, comprising, in a first stage, converting butadiene, in known manner, into alkyl 3-pentenoate by reacting same with carbon monoxide and with an alcohol, at a pressure above atmospheric pressure and at elevated temperature, in the presence of a catalytically effective amount of a catalyst based on cobalt or palladium, and, in a second stage, reacting the pentenoate thus produced with carbon monoxide and an alcohol, also at a pressure above atmospheric pressure and at elevated temperature, in the presence of a catalytically effective amount of cobalt or of a cobalt compound and of a nitrogenous heterocyclic base, also in known manner, and which further comprises:

(a) enriching the alkyl 2-pentenoate content of the reaction mixture originating from the first stage and from which the excess starting materials, the heavy products and all or a portion of the catalyst system have been removed, if appropriate, and (b) introducing the mixture thus enriched in alkyl 2-pentenoate into said second stage.

DETAILED DESCRIPTION OF THE PREFERRED EMBODIMENTS OF THE INVENTION

More particularly according to the present invention, in said first embodiment thereof, a mixture consisting essentially of alkyl 3-pentenoate and alkyl 2-pentenoate is introduced into the so-called second stage reaction.

Such mixture can, of course, also contain alkyl 4-pentenoate and various other constituents such as alkyl pentenoate, pyridine (or nitrogenous heterocyclic base), alkyl methylglutarate, one or more organic diluents and/or solvents, variable amounts of the catalyst system employed during the reaction stage by which the butadiene or mixture containing butadiene is converted into alkyl 3-pentenoate in known manner (first stage) whereby this catalyst system is compatible with the required reaction conditions for the second stage. It will be immediately apparent to one skilled in this art that, when the first stage entails using a cobalt-based catalyst system and a nitrogenous heterocyclic base, it is preferable to rid the reaction mixture of the cobalt emanating from this first stage.

For good results, the alkyl pentenoates will constitute at least 20% by weight and, preferably, at least 40% by weight of the mixture introduced into the second stage.

According to the present invention, it is essential that alkyl 2-pentenoate be present in the mixture introduced into said second stage. Indeed, it has now been determined that this presence has a remarkable influence both on the production efficiency of the required alkyl adipate and on the chemical loss of nitrogenous heterocyclic base. These surprising effects are manifest as soon as the alkyl 2-pentenoate content in the mixture introduced (alkyl 3-pentenoate+2-pentenoate) constitutes at least 5% and preferably at least 10% thereof.

Also for good results, this content will be at least 30%, the maximum being dictated merely by considerations of an economic nature and/or the availability of the alkyl 2-pentenoates.

As also will be immediately apparent to one skilled in this art, the alkyl 3-pentenoates obtained during the first stage can constitute on the order of 90% to 95% (by weight) of the identified products formed. To carry out the present invention, it will thus be appropriate to enrich the raw material introduced into the second stage in said alkyl 2-pentenoates.

Because the alkyl 2-pentenoates are formed during the second stage, a first technique of enriching said raw material in alkyl 2-pentenoate will include at least partial recycling of the alkyl 2-pentenoate formed in said second stage, in which the degree of conversion of the pentenoates will have been deliberately limited.

In practice, the recycling of a mixture of 2-pentenoate and of 3-pentenoate will advantageously be selected, by reason of the difficulties associated with their separation.

A second technique of enriching the raw material in alkyl 2-pentenoate will comprise the preliminary treatment of all or a portion of the alkyl 3-pentenoate emanating from said first stage and/or not converted in the second stage, with a view to isomerizing same to a mixture enriched in alkyl 2-pentenoate, such mixture then being itself introduced into the second stage.

It too is within the scope of the present invention to simultaneously employ the two techniques of enrichment indicated above and, in particular, to recycle all or a portion of the alkyl 2-pentenoate and to treat only that portion of alkyl 3-pentenoate which is not converted during the second stage, when it is desired to operate at a partial degree of conversion of this material in the second stage.

The isomerization can be carried out in various ways which are per se known to the art and, in particular, via the process described in U.S. Pat. No. 4,339,597.

Within the scope of the second technique of enrichment, it is advantageous, nevertheless, to treat the alkyl 3-pentenoate in the presence of cobalt or of a cobalt compound, if appropriate of carbon monoxide and/or of a nitrogenous heterocyclic base, at a temperature above or equal to 150° C., in liquid phase, at a pressure above atmospheric pressure, for a sufficient period of time as to obtain the desired enrichment.

For good results, the reaction temperature for such treatment will be less than or equal to 250° C. and will preferably range from 170° to 200° C.; the total pressure at temperature will be greater than or equal to 20 bar and preferably less than or equal to 300 bar.

Also for good results, the treatment reaction mixture will in most instances be substantially free from alkanol and will be capable of including a nonpolar aprotic organic diluent or solvent.

Exemplary organic solvents useful for such treatment include unsaturated or, preferably, saturated acyclic hydrocarbons, aromatic hydrocarbons and ethers such as tetrahydrofuran and dioxane.

When using a solvent or diluent, the amount thereof will be such that the weight content of the alkyl 3-pentenoate is at least 10% and, preferably, at least 50%.

The presence of a nitrogenous heterocyclic base is not harmful so long as it is present in a minor amount, such that the N/Co ratio is less than or equal to 25.

By "nitrogenous heterocyclic base," as in the case of the first and second stages, compounds well known to this art are intended, notably those described more particularly in European Patent No. 80/0,957.

Pyridine and isoquinoline are exemplary such compounds.

The duration of the treatment (or residence time) may vary over wide limits and will depend to a great extent on the precise nature of the catalyst system and on the other operating conditions selected (presence or otherwise of CO, pressure, temperature, etc.).

In a first embodiment, the alkyl 3-pentenoate is contacted with carbon monoxide in the presence of a cobalt carbonyl, for example of dicobalt octacarbonyl.

The carbon monoxide employed is substantially pure, advantageously in a form which is commercially available. The presence of a minor proportion of hydrogen (<1 vol %) tends to stabilize the catalyst system. Above a threshold on the order of 1% (vol), an interfering or competing hydrogenation reaction of the raw material is likely to occur at the expense of the desired isomerization reaction.

Per this first embodiment of the invention, the reaction mixture will be substantially free from alkanol.

In a second embodiment of the present invention, the alkyl 3-pentenoate is treated in the presence of a cobalt carboxylate, for example cobalt acetate, and of a nitrogenous heterocyclic base, in the absence of carbon monoxide, the atomic ratio N/Co advantageously being selected such that it is compatible with proper progress of the second stage of the reaction and typically ranges from 2 to 25 (approximately).

According to this latter embodiment, the reaction mixture may advantageously contain an alkanol.

In both embodiments the cobalt concentration in the reaction mixture will be at least 0.05 mol/l and advantageously will range from 0.1 to 2 mol/l.

At the end of the treatment or the period of time allocated thereto the pressure is released and, if appropriate, the reaction mixture is cooled.

The mixture thus obtained can be introduced directly, or after removal of the solvent or diluent, into the so-called "second stage" reaction, by which the alkyl adipate is produced in a manner known per se after adjusting the amount of the nitrogenous heterocyclic based, if appropriate of the cobalt concentration and the addition of an alkanol.

The conditions for carrying out said second stage are amply described in the abovementioned prior art, hereby expressly incorporated by reference for more detailed data.

Briefly, within the scope of this second stage, carbon monoxide and an alcohol are reacted in liquid phase with the mixture essentially consisting of alkyl 3-pentenoate and 2-pentenoate in the presence of cobalt or of a cobalt compound and of a nitrogenous heterocyclic based; the reaction temperature typically ranges from 100° to 200° C. and preferably from 130° to 180° C. The total pressure at temperature is generally higher than 50 bar and preferably ranges from 100 to 300 bar. The cobalt concentration can vary over wide limits, for example from 0.05 to 8 mol/l, and preferably from 0.1 to 2 mol/l. The molar ratio of the nitrogenous heterocyclic base to the cobalt typically ranges from 0.5 to 50 and preferably from 2 to 25.

A $C_1$–$C_4$ alkanol and more particularly methanol is preferably employed.

According to the present invention, the mixture introduced into the second stage typically exhibits the following composition, by weight:

(a) alkyl 3-pentenoate, 5%–92%

(b) alkyl 2-pentenoate, 5%–90%

(c) alkyl 4-pentenoate, 1% to 3%

(d) alkyl pentenoate, 1% to 10%

(e) dialkyl adipate, ≈1%

At the end of reaction or of the time allocated thereto, the alkyl adipate is recovered by any appropriate means, for example, eliminating the cobalt from the reaction mixture followed by distillation of the products of reaction and, if appropriate, recycling the unreacted pentenic esters or by phase separation after addition of a nonpolar aprotic solvent followed by the treatment of the resulting two phases, in a manner per se known to this art.

In order to further illustrate the present invention and the advantages thereof, the following specific examples are given, it being understood that same are intended only as illustrative and in nowise limitative.

EXAMPLES 1 TO 3

Control Tests (a) and (b):

These examples relate to the alkoxycarbonylation of the alkyl pentenoates.

Operating technique:

The following reagents were charged into a stainless steel autoclave, 300 ml in capacity, provided with a central magnetic stirrer:

(i) methyl pentenoate(s): 0.58 mol (ii) dicobalt octacarbonyl: 0.012 mol (iii) pyridine: 0.115 mol (iv) methanol: 1.16 mol (v) butylbenzene (internal standard for GPC): 5 g.

Stirring (1,200 rev/min) was started, the autoclave was purged with CO (3×50 bar) and then pressurized to 150 bar with CO (containing 0.5 vol % of $H_2$) and heated to 170° C. The autoclave was maintained under these conditions (170°, 150 bar) throughout the test period. A continuous purging of the gas space was provided by a constant CO inlet flow rate set at 60 l/h (CNTP).

Samples of the reaction mass were withdrawn at regular intervals. After dilution with methanol (q.s. 15 ml), these were analyzed by GPB and ion exclusion liquid chromatography.

The following conventions are hereby established:

P3: methyl 3-pentenoate

P2: methyl 2-pentenoate

P4: methyl 4-pentenoate

Pa: methyl pentanoate

E1: dimethyl adipate

E2: dimethyl 2-methylglutarate

E3: dimethyl ethylsuccinate

E4: dimethyl propylmalonate

Ei=E1+E2+E3+E4

$$L = \frac{E1}{Ei}$$

Pi=P2+P3+P4

Py=pyridine $$DC = \frac{mmol\ substrate\ used - mmol\ substrate\ determined}{mmol\ substrate\ used} \times 100$$

$$RY = \frac{mmol\ product\ determined}{mmol\ substrate\ used} \times 100$$

CY=RY/DC=selectivity $k=-\ln(1-DC)/t$ in $h^{-1}$

C (Py)=number of kg of pyridine decomposed per potential ton of adipic acid determined with the following two assumptions:

(1) reactor batch with DC of 90%

(2) degree of hydrolysis of dimethyl adipate to adipic acid=100%

The Control Test (a) was carried out using methyl 3-pentenoate.

The Control Test (b) was carried out using methyl 2-pentenoate.

Examples 1 to 3 were carried out using a mixture of 3-pentenoate and 2-pentenoate, the 2-pentenoate content of which is reported in Table I below, in which the results obtained are also reported, with t indicating the time required for complete conversion of the pentenoate(s).

TABLE I

| | | | | RY % | | | |
|---|---|---|---|---|---|---|---|
| Example | % P2 | t(min) | K($h^{-1}$) | Pa | El | L % | C(Py) |
| a | 0 | 220 | 1.3 | 9 | 67 | 82 | 10 |
| 1 | 5 | 200 | 1.5 | 9 | 69 | 82 | 9 |
| 2 | 10 | 180 | 1.5 | 9 | 73 | 82 | 9 |
| 3 | 50 | 155 | 1.6 | 9 | 70 | 82 | 8 |
| b | 100 | 180 | 2 | 8 | 72 | 80 | 5 |

EXAMPLES 4 AND 5

These examples illustrate the isomerization of methyl 3-pentenoate.

A test was carried out on a charge containing the following reagents in the autoclave and employing the operating technique described in Example 1 above:

| | | | |
|---|---|---|---|
| (i) 0.58 mol of methyl 3-pentenoate | | | |
| (ii) 0.012 mol of dicobalt octacarbonyl | | | |
| (iii) 0.115 mol of pyridine | } | Example 4 | |
| (iv) 46 ml of toluene | | | |
| or | | | |
| (v) 61 ml of toluene | } | Example 5 | |
| (vi) (absence of pyridine) | | | |

In both examples the reaction temperature was 170° C., the pressure was 150 bar, the rate of stirring was 1,200 rev/min and the carbon monoxide inlet flow rate was 60 l/h (CNTP).

The results obtained are reported in Table II below, in which T represents the reaction time.

TABLE II

| | Py | | DC(P3) | RY % | | | |
|---|---|---|---|---|---|---|---|
| Example | (mol) | T(h) | (%) | P2 | P4 | Pa | Ei |
| 4 | 0.115 | 2 | 31 | 70.6 | 6.3 | 12.9 | 2.2 |
| 5 | 0 | 3 | 56.5 | 74.2 | 6.8 | 7.7 | 3.0 |

EXAMPLES 6 AND 7

These examples illustrate the isomerization of methyl 3-pentenoate.

The following reagents were charged into a 125-ml capacity autoclave made of Hastelloy® B2:

(i) 0.1 mol of methyl 3-pentenoate
(ii) 0.004 mol of cobalt acetate
(iii) 0.02 mol of pyridine
(iv) 8 ml of methanol (Example 6) or
(v) 10 ml of toluene (Example 7)

The autoclave was closed, purged with argon 5 and heated to 200° C. with agitation (by shaking). After hours of reaction at this temperature, it was cooled. The reaction mass was withdrawn, diluted with methanol and analyzed by gas phase chromatography.

The results obtained are reported in Table III below:

TABLE III

| | | DC(P3) | RY % | | |
|---|---|---|---|---|---|
| Example | Solvent | (%) | P2 | P4 | Pa |
| 6 | methanol | 50 | 68 | 1.6 | 6 |
| 7 | toluene | 21 | 30 | 3 | 8 |

EXAMPLE 8

This example illustrates an isomerization—alkoxycarbonylation sequencing.

The following reagents were charged into a stainless steel autoclave 300 ml in capacity, provided with a central magnetic stirrer:

(i) 0.58 mol of methyl 3-pentenoate
(ii) 0.012 mol of dicobalt octacarbonyl
(iii) 61 ml of toluene
(iv) 5 g of n-butylbenzene (internal standard).

The reaction was conducted for 90 min under the conditions of Example 1 above. The autoclave was then cooled and depressurized. Analysis of an aliquot fraction of the reaction mass gave the following results:

DC P3=43%
RY P2=77%
RY P4=8.3%
RY Pa=8.2%

The reaction mass contained, in particular,

| | |
|---|---|
| (a) 0.33 mol of P3 (61%) | } Pi normalized to 100% |
| (b) 0.19 mol of P2 (35%) | |
| (c) 0.02 mol of P4 (4%) | |

The following materials were added to this reaction mass which was retained in the autoclave:

methanol (26 ml, 0.638 mol)
pyridine (12, ml, 0.148 mol)

The autoclave was then closed, purged with carbon monoxide (3×10 bar) and then heated to 170° C. under 150 bar of CO [containing 0.5 vol % of hydrogen].

The stirring rate was 1,200 rev/min.

The carbon monoxide was introduced at a constant flow rate of 60 l/h (CNTP).

After 140 min of reaction, the autoclave was cooled and degassed. The reaction mass was then drawn off and analyzed by gas phase chromatography and ion exclusion liquid chromatography.

The results were as follows:

| | | | |
|---|---|---|---|
| DC (Pi) | = | 99% | |
| k | = | 2 h$^{-1}$ | |
| CY (E1) | = | 70% | } in relation to the Pi of the crude reaction product from the isomerization stage |
| CY (E2) | = | 11% | |
| CY (E3) | = | 4% | |
| CY (Pa) | = | 8% | |
| C(Py) | = | 4 | |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an alkyl adipate comprising (i) enriching an alkyl 3-pentenoate containing raw material to at least 5% alkyl 2-pentenoate by addition of alkyl 2-pentenoate to form an admixture, and
  (ii) reacting said admixture with carbon monoxide and an alcohol, at elevated temperature, under superatmospheric pressure and in the presence of a catalytically effective amount of cobalt or a cobalt compound and a nitrogenous heterocyclic base.

2. The process as defined by claim 1, said alkyl 2-pentenoate comprising at least 10% of said admixture thereof.

* * * * *